United States Patent [19]
Goodby et al.

[11] Patent Number: 5,595,682
[45] Date of Patent: Jan. 21, 1997

[54] LIQUID CRYSTAL COMPOUNDS, MIXTURES AND DEVICES

[75] Inventors: John W. Goodby; Kenneth J. Toyne; Christopher J. Booth, all of Hull, United Kingdom

[73] Assignees: The Secretary of State for Defence in Her Britannic Majesty's Government of the United Kingdom of Great Britain And Northern Ireland; Defence Research Agency, both of United Kingdom

[21] Appl. No.: 416,897

[22] PCT Filed: May 28, 1993

[86] PCT No.: PCT/GB93/01133

§ 371 Date: Apr. 18, 1995

§ 102(e) Date: Apr. 18, 1995

[87] PCT Pub. No.: WO93/25631

PCT Pub. Date: Dec. 23, 1993

[30] Foreign Application Priority Data

Jun. 10, 1992 [GB] United Kingdom .................. 9212334

[51] Int. Cl.[6] .......................... C09K 19/52; C09K 19/20; C09K 19/12; G02F 1/13
[52] U.S. Cl. ................. 252/299.01; 252/299.61; 252/299.63; 252/299.64; 252/299.65; 252/299.66; 252/299.67; 349/182
[58] Field of Search .................. 252/299.01, 299.64, 252/299.65, 299.66, 299.67, 299.61, 299.63; 359/103

[56] References Cited

FOREIGN PATENT DOCUMENTS 0197677  3/1986  European Pat. Off. .
2612182  9/1988  France .

OTHER PUBLICATIONS

Liquid Crystals, vol. 11., No. 1, Jan. 1992, London GB pp. 135–143, J. W. Goodby et al 'the effect of structural changes in the molecular core and periphery on the liquid–crystalline properties et al'.

*Primary Examiner*—Shean C. Wu
*Attorney, Agent, or Firm*—Nixon & Vanderhye

[57] ABSTRACT

Liquid crystal compounds having the formula (I)

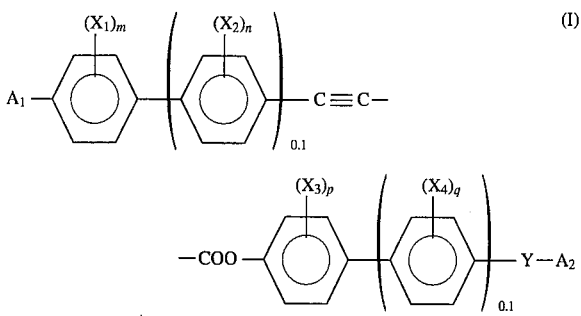

in which $A_1$ is alkyl, alkoxy or alkenyl; $X_1$, $X_2$, $X_3$ and $X_4$ are independently halogens, m, n, p and q are independently 0, 1, 2, 3 or 4 such that $m+n+p+q \neq 0$; Y is O or COO; and $A_2$ is an end group of the formula (II),

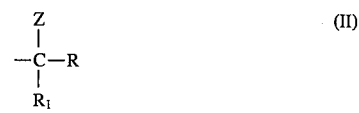

where Z is halogen, $CH_3$, CN, $CF_3$ or, $CHF_2$; R is a linear or branched alkyl group or H; and $R_1$ is a linear or branched alkyl group or H.

11 Claims, 8 Drawing Sheets

LIQUID CRYSTAL COMPOUNDS, MIXTURES AND DEVICES

This application is a 371 of PCT/GB93/01133 filed May 23, 1993.

This invention relates to novel liquid crystal compounds, liquid crystal materials containing them and their inclusion in liquid crystal devices.

Liquid crystals can exist in various phases. In essence there are three different classes of liquid crystalline material, each possessing a characteristic molecular arrangement. These classes are nematic, cholesteric and smectic. A wide range of smectic phases exists, for example smectic A and smectic C. Some liquid crystal materials possess a number of liquid crystal phases on varying the temperature, others have just one phase. For example, a liquid crystal material may show the following phases on being cooled from the isotropic phase:—isotropic—nematic—smectic A—smectic C—solid. If a material is described as being smectic A then it means that the material possesses a smectic A phase over a useful working temperature range.

Compounds such as:

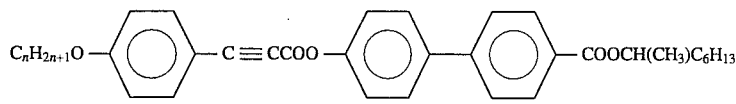

are described in J. Am. Chem. Soc., 1989, 111, 8119–8125 by J. W. Goodby et. al., where n ranges from 8 to 16. At long n-alkoxy chain lengths the series exhibits a novel variation of mesophase behaviour to which a smectic A* phase was assigned. Some of the materials also appeared to exhibit two further mesophases.

According to this invention there are provided compounds having a general formula I

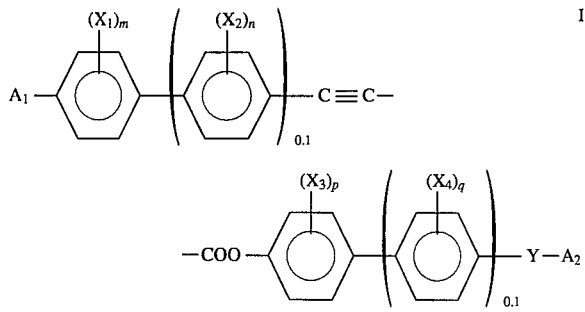

in which $A_1$ is selected from alkyl, alkoxy or alkenyl; $X_1$, $X_2$, $X_3$ and $X_4$ are independently selected from the halogen group; m, n, p and q are independently 0, 1, 2, 3 or 4 such that $m+n+p+q \neq 0$; Y is selected from O and COOO; $A_2$ is an end group of formula II

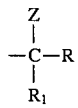

where Z is selected from halogen, $CH_3$, CN, $CF_3$, $CHF_2$; R is a linear or branched alkyl group or H; $R_1$ is a linear or branched alkyl group or H.

Preferably $A_1$ is $C_{3-20}$, more preferably $C_{6-16}$, even more preferably $C_{9-15}$.

Preferably $A_2$ is a chiral end group.

Preferably R is $C_{2-15}$, more preferably $C_{3-10}$, even more preferably $C_{5-7}$.

Preferably $R_1$ is $C_{1-5}$, more preferably H.

Preferably Z is $CH_3$ or CN.

Preferably X is F.

Preferably each of m n, p and/or q is independently 1 or 2 such that $m+n+p+q=1$ or 2.

Compounds of Formula I can be included in a material, the material being a mixture of compounds.

The materials of this aspect of the invention may be used in many of the known forms of liquid crystal display devices, for example chiral smectic electrooptic devices. Such a device may comprise a layer of liquid structures and surface treated to align liquid crystal material molecules. The liquid crystal mixtures may have applications in ferroelectric, ferrielectric (M. Johno et al., Japan Display, 1989, 22), antiferroelectric, thermochromic and electroclinic devices; they may also lead to the formation of frustrated liquid crystal phases. Frustrated phases arise from mesophases possessing double twist structures which means that space cannot be filled uniformly and the phase is stabilised via a lattice of defects. Frustrated phases can also arise from the competition between helical and layer structures, an example of which is the smectic A* analogue of the Abrikson flux phase as described by J. W. Goodby, M. A. Waugh, S. M. Stein, E. Chin, R. Pindak, Nature, 1989, 337, 449; A. J. Slaney and J. W. Goodby, J. Mater. Chem. 1991, 1, 5. The competition between helical and layer structures leads to defects being formed which again stabilise the phase.

Ferroelectric smectic liquid crystal materials, which can be produced by mixing an achiral host and a chiral dopant, use the ferroelectric properties of the tilted chiral smectic C, F, G, H, I, J and K phases. The chiral smectic C phase is denoted $S_c^*$ with the asterisk denoting chirality. The $S_c$ phase is generally considered to be the most useful as it is the least viscous. Ferroelectric smectic liquid crystal materials should ideally posses the following characteristics: low viscosity, controllable spontaneous polarisation (Ps) and an $S_c$ phase that persists over a broad temperature range, which should include ambient temperature and exhibits chemical and photochemical stability. Materials which possess these characteristics offer the prospect of very fast switching liquid crystal containing devices. Some applications of ferroelectric liquid crystals are described by J. S. Patel and J. W. Goodby in Opt. Eng., 1987, 26, 273.

The electroclinic effect, first described by S. Garoff and R. Meyer, Phys. Rev. Lett., 38, 848, 1977, usually occurs in the smectic A phase. Unlike ferroelectric devices, the liquid crystal material in electroclinic devices is not bistable. The liquid crystal director within an EC device responds almost linearly to an applied electric field. Electroclinic devices are suitable for various applications including spatial light modulators.

Chadani et al., Jpn. J. Appl. Phys., 27, L 729, 1988; Jpn. J. Appl. Phys., 28, L 1261, 1989; Jpn. J. Appl. Phys., 28, L 1265, 1989, first described and antiferroelectric effect which is a tri-stable switching state occurring in a liquid crystal phase designated as $SmC_A^*$. For example, when ferroelectric layers are stacked so that an the polarisation vectors in sequential layers oppose one another then an antiferrelectric phase is obtained.

For a review of thermochromism in liquid crystals see J. G. Grabmaier in 'Applications of Liquid Crystals', G. Meier, E. Sackmann and J. G. Grabmaier, Springer-Verlag, Berlin and New York, 1975, pp 83–158.

For all the above applications it is not usual for a single compound to exhibit all of the properties highlighted, for example ferroelectric smectic liquid crystal materials generally consist of a mixture of compounds which when mixed together induce a chiral tilted smectic phase chiral dopants are added to a liquid crystalline mixture in order to induce the smectic mixture to become chiral smectic and to induce a Ps in the material, or if the material already possesses a Ps then the introduction of a chiral dopant should result in a change of value for Ps.

BRIEF DESCRIPTION OF THE DRAWINGS

The invention will now be described by way of example only with reference to the accompanying drawings of which.

DETAILED DESCRIPTION OF THE INVENTION

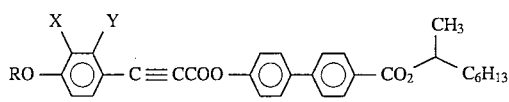
VII

Figure 1:
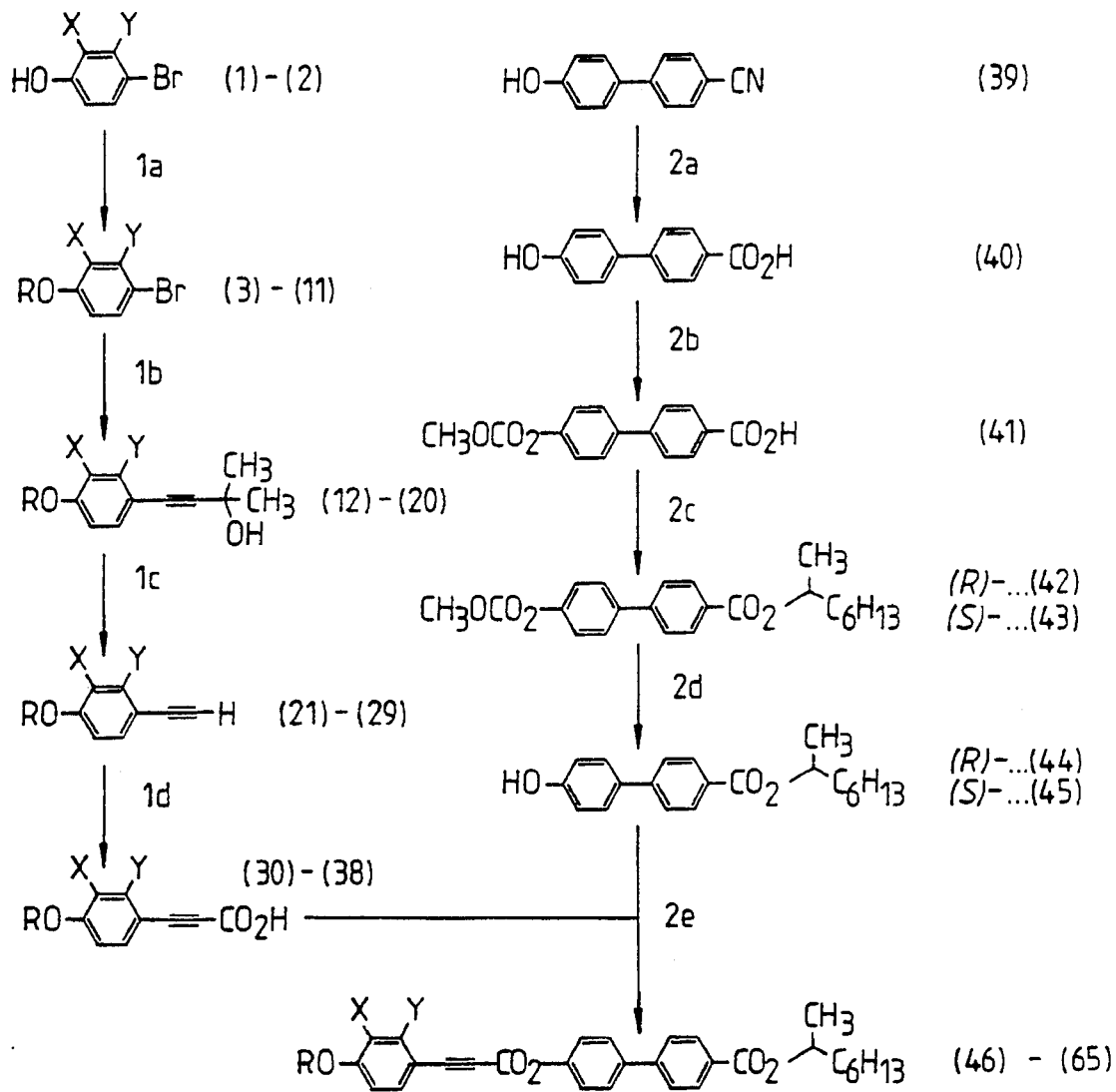
FIG. 1 describes a synthetic route for the preparation of example compounds 46 to 65, i.e. compounds of general formula VII where X and Y are described in Tables 5 and 6.

Reagents used in the synthetic route of FIG. 1 are shown in Route 1.

Compound 1 is synthesized from 3-fluorophenol (Fluorochem Ltd) by a fast bromination at −5° C. ($Br_2$, acetic acid). Compound 2 is commercially available from Fluorochem Ltd. Compound 39 is a commercially available liquid crystal precursor from Merck.

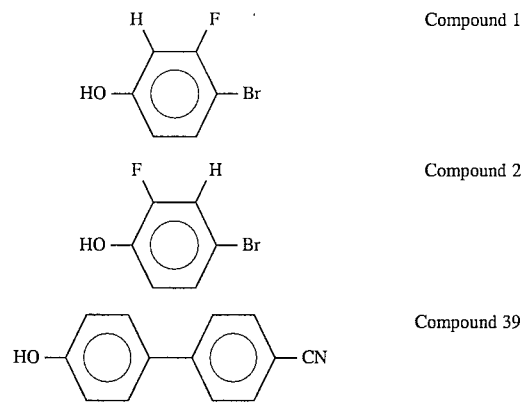

Route 1

The steps are identified below:

1a RBr, $K_2CO_3$, butanone, reflux.

1b 3-methylbut-1-yn-3-ol, $Pd(PPh_3)_4$, CuI, $(^iPr)_2NH$, $N_2$, reflux.

1c KOH, toluene, $N_2$, reflux.

1d (i) BuLi, THF, $N_2$, −10° C; (ii) $CO_2$(s), THF, −10° C. to RT; (iii) HCl (conc).

2a $H_2SO_4$, AcOH, $H_2O$, reflux.

2b (i) NaOH, $CH_3OCOCl$, $H_2O$, 0° C.; (ii) 1:1 Hcl:$H_2O$, pH=5.

2c (R)- or (S)-2-octanol, diethyl azodicarboxylate, $PPh_3$, THF, $N_2$, RT.

2d EtOH, $NH_3$ (aq), RT.

2e Dicyclohexylcarbodiimide, 4-N,N-dimethylaminopyridine, $CH_2Cl_2$, RT.

This route allows the configuration about the chiral carbon to be easily controlled.

COMPOUND 3

Preparation of 1-Bromo-4-dodecyloxy-2-fluorobenzene

1-Bromodecane (12.01 g, 48.2 mmol) in butanone (20 ml) was added dropwise to a stirred, refluxing mixture of 4-bromo-3-fluorophenol (1) (9.04 g, 47.4 mmol), potassium carbonate (10.12 g, 73.2 mmol) and butanone (100 ml). The resulting reaction mixture was refluxed for a further 20 hours. The cooled reaction mixture was then filtered to remove the excess potassium carbonate and precipitated potassium bromide. The filtrate was washed with 5% (v/v) sodium hydroxide (2×50 ml) then water (50 ml) and the organic layer then dried ($MgSO_4$), filtered and evaporated under reduced pressure to give a colourless oil which was purified by column chromatography [silica gel: 1:1 dichloromethane-petrol (bp 40°–60° C.)] to give a colourless liquid. This was then dried in vacuo ($P_2O_5$, 0.20 mm Hg, RT, 5 h).

Yield=16.73 g, (98%)

Compounds 3–11 have general formula III, see Table 1.

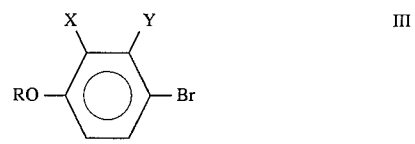
III

COMPOUND 4

Preparation of 1-Bromo-2-fluoro-4-tridecyloxybenzene

This was prepared using a similar method to that described for compound 3. Quantities: compound 1 (4.02 g, 21.1 mmol), 1-bromotridecane (6.11 g, 23.2 mmol), potassium carbonate (5.22 g, 37.8 mmol) and butanone (115 ml).

Yield=6.62 g, (84%) mp=26°=27° C.

COMPOUND 5

Preparation of 1-Bromo-2-fluoro-4-tetradecyloxybenzene

This was prepared using a similar method to that described for compound 3. Quantities: compound 1 (4.03 g, 21.1 mmol), 1-bromotetradecane (6.41 g, 23.1 mmol), potassium carbonate (5.59 g, 40.5 mmol) and butanone (115 ml).

Yield=7.48 g, 92%) mp=30°–31° C.

COMPOUND 6

Preparation of 1-Bromo-2-fluoro-4-pentadecyloxybenzene

This was prepared using a similar method to that described for compound 3. Quantities: compound 1 (2.31 g, 12.1 mmol), 1-bromopentadecane (3.97 g, 13.6 mmol), potassium carbonate (2.97 g, 21.5 mmol) and butanone (80 ml).

Yield=4.35 g, (90%) mp=32°–36° C.

COMPOUND 7

Preparation of 1-Bromo-4-dodecyloxy-3-fluorobenzene

This was prepared using a similar method to that described for compound 3. Quantities: compound 2 (6.00 g, 31.4 mmol), 1-bromododecane (8.23 g, 33.1 mmol), potassium carbonate (5.67 g, 40.9 mmol) and butanone (100 ml).

Yield=11.11 g, (99%)

COMPOUND 8

Preparation of 1-Bromo-3-fluoro-4-tridecyloxybenzene

This was prepared using a similar method to that described for compound 3. Quantities: compound 2 (6.01 g, 31.5 mmol), 1-bromotridecane (8.75 g, 33.2 mmol), potassium carbonate (5.67 g, 40.9 mmol) and butanone (100 ml).

Yield=11.69 g, (99%) mp=37°–39° C.

COMPOUND 9

Preparation of 1-Bromo-3-fluoro-4-tetradecyloxybenzene

This was prepared using a similar method to that described for compound 3. Quantities: compound 2 (6.02 g, 31.5 mmol), 1-bromotetradecane (9.15 g, 33.0 mmol), potassium carbonate (5.67 g, 40.9 mmol) and butanone (100 ml).

Yield=11.82 g, (97%) mp=28°–29° C.

COMPOUND 10

Preparation of 1-Bromo-3-fluoro-4-pentadecyloxybenzene

This was prepared using a similar method to that described for compound 3. Quantities: compound 2 (5.04 g, 26.4 mmol), 1-bromotetradecane (8.15 g, 27.9 mmol), potassium carbonate (5.65 g, 40.9 mmol) and butanone (120 ml).

Yield=9.54 g, (90%) mp=40°–43° C.

COMPOUND 11

Preparation of 1-Bromo-3-fluoro-4-hexadecyloxybenzene

This was prepared using a similar method to that described for compound 3. Quantities: compound 2 (5.02 g, 26.3 mmol), 1-bromohexadecane (8.56 g, 28.0 mmol), potassium carbonate (5.19 g, 37.6 mmol) and butanone (100 ml).

Yield=10.09 g, (92%) mp=41°–43° C.

COMPOUND 12

Preparation of 4-Dodecyloxy-2-fluoro-1-(3-hydroxy-3-methylbut-1-ynyl)benzene A stream of dry nitrogen was bubbled through a stirred, dark green mixture of compound 3 (5.00 g, 12.9 mmol), palladium (O) tetrakis(triphenylphosphine) (1.02 g, 0.89 mmol), copper (I) iodide (0.11 g, 0.58 mmol) and dry di-isopropylamine (30 ml) for a period of 10 min. A solution of 3-methylbut-1-yn-3-ol (2.54 g, 30.2 mmol) in dry di-isopropylamine (10 ml) was added dropwise at room temperature; the reaction mixture turned deep orange-brown. The reaction was then heated for 4 hours under gentle reflux under nitrogen. The cooled reaction was filtered through a pad of 'Hyflo-supercel' and water (50 ml) added to the filtrate. The crude product was then extracted using diethyl ether (3×50 ml); the combined ethereal extracts were then washed with brine (50 ml), dried (MgSO$_4$), filtered and evaporated to give a brown oil. This was then purified by flash chromatography [fine mesh silica gel; 9:1 dichloromethane-petrol (bp 40°–60° C.)] to give a brown solid which was recrystallised from cyclohexane and dried in vacuo (P$_2$O$_5$, 0.30 mm Hg, RT, 4 hours).

Yield=4.70 g, (93%) mp=43°–46° C.

Compound 12–20 have general formula IV, see Table 2.

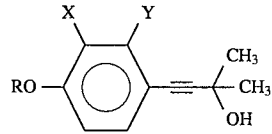

IV

COMPOUND 13

Preparation of 2-Fluoro-1-(3-hydroxy-3-methylbut-1-ynyl)-4-tridecyloxybenzene This compound was prepared using a similar method to that described for compound 12. Quantities: compound 4 (5.18 g, 13.9 mmol), palladium (O) tetrakis(triphenylphosphine) (1.03 g, 0.91 mmol), copper (I) iodide (0.68 mmol), 3-methylbut-1-yn-3-ol (2.54 g, 30.2 mmol) and di-isopropylamine (50 ml). The crude product was purified by flash chromatography [fine mesh silica gel; 10% (v/v) ethyl acetate in petrol (bp 40°–60° C.)] to give a yellow solid which was recrystallized from cyclohexane and dried in vacuo (P$_2$O$_5$, 0.20 mm Hg, RT, 18 hours).

Yield=3.17 g, (58%) mp=35°–36° C.

COMPOUND 14

Preparation of 2-Fluoro-1-(3-hydroxy-3-methylbut-1-ynyl)-4-tetradecyloxybenzene This compound was prepared using a similar method to that described for compound 12. Quantities: compound 4 (5.40 g, 13.95 mmol), palladium (O) tetrakis(triphenylphosphine) (1.03 g, 0.89 mmol), copper (I) iodide (0.14 g, 0.74 mmol), 3-methylbut-1-yn-3-ol (2.55 g, 30.4 mmol) and di-isopropylamine (50 ml). The crude product was purified by flash chromatography [fine mesh silica gel; 10% (v/v) ethyl acetate in petrol (bp 40°–60° C.)] to give a yellow solid which was recrystallized from cyclohexane and dried in vacuo (P$_2$O$_5$, 0.20 mm Hg, RT, 18 hours).

Yield=2.34 g, (43%) mp=44°–45° C.

COMPOUND 15

Preparation of 2-Fluoro-1-(3-hydroxy-3-methylbut-1-ynyl)-4-pentadecyloxybenzene This compound was prepared using a similar method to that described for compound 12. Quantities: compound 6 (4.22 g, 10.5 mmol), palladium (O) tetrakis(triphenylphosphine) (1.0 g, 0.87 mmol), copper (I) iodide (0.14 g, (0.74 mmol), 3-methybut-1-yn-3-ol (1.90 g, 22.6 mmol) and di-isopropylamine (50 ml). The crude product was purified by flash chromatography [fine mesh silica gel; 5% (v/v) ethyl acetate in petrol (bp 40°–60° C.)] to give an orange oil which crystallised on standing. This was recrystallized from cyclohexane and dried in vacuo (P$_2$O$_5$, 0.20 mm Hg, RT, 6 hours).

Yield=1.57 g, (37%) mp=40°–41° C.

COMPOUND 16

Preparation of 3-Fluoro-4-dodecyloxy-1-(3-hydroxy-3m-ethylbut-1-ynyl)benzene This compound was prepared using a similar method to that described for compound 12. Quantities: compound 7 (5.00 g, 13.9 mmol), palladium (O) tetrakis(triphenylphosphine) (1.03 g, 0.89 mmol), copper (I) iodide (0.12 g, (0.63 mmol), 3-methybut-1-yn-3-ol (2.54 g, 30.2 mmol) and di-isopropylamine (40 ml). The crude product was purified by flash chromatography [fine mesh silica gel; 1:1 dichloromethane-petrol (bp 40°–60° C.)]; to give an orange solid which was recrystallized from cyclohexane and dried in vacuo (P$_2$O$_5$, 0.30 mm Hg, RT, 10 hours).

Yield=3.58 g, (71%) mp=30°–32° C.

COMPOUND 17

Preparation of 3-Fluoro-1-(3-hydroxy-3-methylbut-1-ynyl)-4-tridecyloxybenzene This compound was prepared using a similar method to that described for compound 12. Quantities: compound 8 (5.20 g, 13.9 mmol), palladium (O) tetrakis(triphenylphosphine) (1.03 g, 0.89 mmol), copper (I) iodide (0.14 g, (0.74 mmol), 3-methybut-1-yn-3-ol (2.54 g, 30.2 mmol) and di-isopropylamine (40 ml). The crude product was purified by flash chromatography [fine mesh silica gel; 10% (v/v) ethyl acetate in petrol (bp 40°–60° C.)]; to give a yellow solid which was recrystallized from cyclohexane and dried in vacuo (P$_2$O$_5$, 0.20 mm Hg, RT, 20 hours).

Yield=4.63 g, (88%) mp=46°–48° C.

COMPOUND 18

Preparation of 3-Fluoro-1-(3-hydroxy-3-methylbut-1-ynyl)-4-tetradecyloxybenzene This compound was prepared using a similar method to that described for compound 12. Quantities: compound 9 (5.40 g, 13.9 mmol), palladium (O) tetrakis(triphenylphosphine) (1.05 g, 0.91 mmol), copper (I) iodide (0.13 g, (0.68 mmol), 3-methybut-1-yn-3-ol (2.54 g, 30.2 mmol) and di-isopropylamine (40 ml). The crude product was purified by flash chromatography [fine mesh silica gel; 10% (v/v) ethyl acetate in petrol (bp 40°–60° C.)]; the white solid recrystallized from cyclohexane and dried in vacuo (P$_2$O$_5$, 0.40 mm Hg, RT, 24 hours).

Yield=4.16 g, (76%) mp=45°–46° C.

COMPOUND 19

Preparation of 3-Fluoro-1-(3-hydroxy-3-methylbut-1-ynyl)-4-pentadecyloxybenzene This compound was prepared using a similar method to that described for compound 12. Quantities: compound 10 (5.58 g, 13.9 mmol), palladium (O) tetrakis(triphenylphosphine) (1.02 g, 0.88 mmol), copper (I) iodide (0.11 g, (0.58 mmol), 3-methybut-1-yn-3-ol (2.54 g, 30.2 mmol) and di-isopropylamine (50 ml). The crude product was purified by flash chromatography [fine mesh silica gel; 5% (v/v) ethyl acetate in petrol (bp 40°–60° C.)]; the yellow solid was recrystallized from cyclohexane and dried in vacuo (P$_2$O$_5$, 0.20 mm Hg, RT, 72 hours).

Yield=5.05 g, (90%) mp=54°–55° C.

COMPOUND 20

Preparation of 3-Fluoro-4-hexadecyloxy-1-(3-hydroxy-3-methylbut-1-ynyl)benzene This compound was prepared using a similar method to that described for compound 12. Quantities: compound 11 (6.02 g, 14.5 mmol), palladium (O) tetrakis(triphenylphosphine) (1.01 g, 0.9 mmol), copper (I) iodide (0.17 g, 0.9 mmol), 3-methybut-1-yn-3-ol (2.46 g, 29.2 mmol) and di-isopropylamine (60 ml). The crude product was purified by flash chromatography [fine mesh silica gel; 5% (v/v) ethyl acetate in petrol (bp 40°–60° C.)]; the yellow solid obtained was recrystallized from cyclohexane and dried in vacuo (P$_2$O$_5$, 0.20 mm Hg, RT, 5 hours).

Yield=4.68 g, (77%) mp=49°–50° C.

COMPOUND 21

4-Dodecyloxy-1-ethynyl-2-fluorobenzene

Compound 12 (3.85 g, 10.6 mmol), potassium hydroxide (0.62 g, 11.1 mmol) and toluene (100 ml) were stirred and heated under reflux under nitrogen for 2 hours. The acetone and toluene azeotrope was removed periodically via a Dean and Stark receiver and replaced with an equal volume of toluene. The cooled reaction mixture was poured onto water (100 ml) and the organic phase separated. The aqueous phase was then washed with diethyl ether (3×50 ml) and recombined with the organic layer before being washed with brine (50 ml), dried (MgSO$_4$), filtered and evaporated to give an orange oil. This was purified by flash chromatography [fine mesh silica gel; petrol (bp 40°–60° C.)] the yellow solid obtained was recrystallised (cyclohexane) and dried in vacuo (P$_2$O$_5$, 0.30 mm Hg, RT, 5 hours).

Yield=2.28 g (71%) mp=35°–36° C.

Compound 21-19 have general formula V, see Table 3.

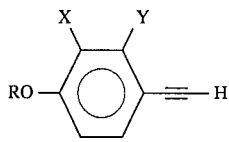

V

COMPOUND 22

1-Ethynyl-2-fluoro-4-tridecyloxybenzene

This compound was prepared using a similar method to that described for compound 21. Quantities: compound 13 (3.08 g, 8.19 mmol) potassium hydroxide (0.53 g, 9.45 mmol and toluene (80 ml). The crude product was purified by flash chromatography [fine mesh silica gel; 9:1 dichloromethane-petrol (bp 40°–60° C.)]; the brown solid obtained was recrystallized from cyclohexane and dried in vacuo ($P_2O_5$, 0.10 mm Hg, 40° C., 7 hours).

Yield=1.89 g, (72%) mp=40°–41° C.

COMPOUND 23

1-Ethynyl-2-fluoro-4-tetradecyloxybenzene

This compound was prepared using a similar method to that described for compound 21. Quantities: compound 14 (2.35 g, 6.02 mmol) potassium hydroxide (0.39 g, 6.95 mmol and toluene (70 ml). The crude product was purified by flash chromatography [fine mesh silica gel; dichloromethane]; the yellow solid obtained was recrystallised from cyclohexane and dried in vacuo ($P_2O_5$, 0.10 mm Hg, 40° C., 3 hours).

Yield=1.28 g, (64%) mp=41°–42° C.

COMPOUND 24

1-Ethynyl-2-fluoro-4-pentadecyloxybenzene

This compound was prepared using a similar method to that described for compound 21. Quantities: compound 15 (1.53 g, 3.8 mmol) potassium hydroxide (0.26 g, 4.6 mmol and toluene (100 ml). The crude product was purified by flash chromatography [fine mesh silica gel; dichloromethane]; the yellow solid obtained was recrystallised from cyclohexane and dried in vacuo ($P_2O_5$, 0.30 mm Hg, RT, 18 hours).

Yield=1.17 g, (88%) mp=41°–42° C.

COMPOUND 25

1-Ethynyl-3-fluoro-4-dodecyloxybenzene

This compound was prepared using a similar method to that described for compound 21. Quantities: compound 16 (3.49 g, 9.64 mmol) potassium hydroxide (0.62 g, 11.07 mmol and toluene (100 ml). The crude product was purified by flash chromatography [fine mesh silica gel; 9:1 dichloromethane-petrol (bp 40°–60° C.)]; the yellow solid obtained was dried in vacuo ($P_2O_5$, 0.40 mm Hg, RT, 6 hours).

Yield=2.65 g, (90%) mp—not recorded

COMPOUND 26

1-Ethynyl-3-fluoro-4-tridecyloxybenzene

This compound was prepared using a similar method to that described for compound 21 Quantities: compound 17 (4.56 g, 12.2 mmol) potassium hydroxide (0.76 g, 13.5 mmol and toluene (100 ml). The crude product was purified by flash chromatography [fine mesh silica gel; 9:1 dichloromethane-petrol (bp 40°–60° C.]; the yellow solid obtained was dried in vacuo ($P_2O_5$, 0.40 mm Hg, RT, 4 hours).

Yield=3.54 g, (91%) mp=39°–41° C.

COMPOUND 27

1-Ethynyl-3-fluoro-4-tetradecyloxybenzene

This compound was prepared using a similar method to that described for compound 21. Quantities: compound 18 (4.06 g, 10.4 mmol) potassium hydroxide (0.62 g, 11.1 mmol and toluene (100 ml). The crude product was purified by flash chromatography [fine mesh silica gel; 9:1 dichloromethane-petrol (bp 40°–60° C.)]; the yellow solid obtained was dried in vacuo ($P_2O_5$, 0.35 mm Hg, RT, 6 hours).

Yield=3.08 g, (89%) mp=34°–35° C.

COMPOUND 28

1-Ethynyl-3-fluoro-4-pentadecyloxybenzene

This compound was prepared using a similar method to that described for compound 21. Quantities: compound 19 (4.99 g, 12.35 mmol) potassium hydroxide (0.73 g, 13.01 mmol and toluene (100 ml). The crude product was purified by flash chromatography [fine mesh silica gel; 9:1 dichloromethane-petrol (bp 40°–60° C.)]; the orange solid obtained was recrystallised from cyclohexane and dried in vacuo ($P_2O_5$, 0.20 mm Hg, 40° C., 5 hours).

Yield=2.69 g, (68%) mp=45°–47° C.

COMPOUND 29

1-Ethynyl-3-fluoro-4-hexadecyloxybenzene

This compound was prepared using a similar method to that described for compound 21. Quantities: compound 20 (4.61 g, 8.8 mmol) potassium hydroxide (0.52 g, 9.2 mmol) and toluene (120 ml). The crude product was purified by flash chromatography [fine mesh silica gel; dichloromethane]; the yellow solid obtained was dried in vacuo ($P_2O_5$, 0.30 mm Hg, RT, 18 hours).

Yield=2.89 g, (91%) mp=37°–39° C.

COMPOUND 30

3-(2-Fluoro-4-dodecyloxyphenyl)propiolic Acid

Butyllithium (2.8 ml, 2.5M in hexanes) was added dropwise to a stirred, cooled (−78° C.) solution of compound 21 (2.10 g, 6.91 mmol) in dry thf (100 ml) under nitrogen. The resulting solution was kept at −78° C. for a further 1.5 hours before being poured onto a stirred slurry of crushed 'Cardice' and dry thf (100 ml) and allowed to warm to room temperature overnight. The solution was acidified with concentrated hydrochloric acid and water (100 ml) added. The product was extracted with diethyl ether (3×50 ml). The combined ethereal extracts were then washed with brine (50 ml), dried (MgSO$_4$), filtered and evaporated to give a yellow solid. The product was purified by flash chromatography [fine mesh silica gel; dichloromethane (initially) and 9:1 dichloromethane-methanol (finally)]. Two fractions were obtained and recrystallised from cyclohexane and dried in vacuo ($P_2O_5$, 0.30 mm Hg, RT, 10 hours), the first proving to be unreacted compound 21.

Yield=0.87 g, (36%) mp—not recorded

Compounds 30–38 have general formula VI, see Table 4.

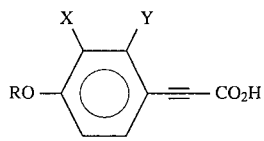

VI

COMPOUND 21

3-(2-Fluoro-4-tridecyloxyphenyl)propiolic Acid

Butyllithium (2.4 ml, 2.5M in hexanes) was added dropwise to a stirred, cooled (−10° C.) solution of compound 22 (1.80 g, 5.66 mmol) in dry thf (40 ml) under nitrogen. The reaction was stirred for a further 10 min at −10° C. before being poured onto a stirred slurry of crushed 'Cardice' and dry thf (20 ml) with stirring and allowed to warm to room temperature. The solution was acidified with concentrated hydrochloric acid and then diluted with water (100 ml). The organic phase was then separated and the aqueous phase washed with diethyl ether (2×50 ml). The combined organic phases were then washed with brine (50 ml), dried ($MgSO_4$), filtered and evaporated to give a brown liquid. The product was purified by flash chromatography [fine mesh silica gel; dichloromethane (initially) and 9:1 dichloromethane-methanol (finally)]; to give a brown solid which was recrystallised from cyclohexane and dried in vacuo ($P_2O_5$, 0.20 mm Hg, 40° C., 5 hours).

Yield=0.84 g, (41%) mp=98°–99° C.

COMPOUND 32

3-(2-Fluoro-4-tetradecyloxyphenyl)propiolic Acid

This compound was prepared using a similar method to that described for compound 31. Quantities: compound 23 (1.21 g, 3.6 mmol), butyllithium (1.5 ml, 2.5M in hexanes) and dry thf (35 ml). The crude product was purified by flash chromatography [fine mesh silica gel; dichloromethane (initially) and 9:1 dichloromethane-methanol (finally)]; to give a brown solid which was recrystallised (ethanol) and dried in vacuo ($P_2O_5$, 0.20 mm Hg, 40° C., 5 hours).

Yield=0.97 g, (71%) mp=90°–109(dec)° C.

COMPOUND 33

3-(2-Fluoro-4-pentadecyloxyphenyl)propiolic Acid

This compound was prepared using a similar method to that described for compound 31. Quantities: compound 24 (1.16 g, 3.4 mmol), butyllithium (1.4 ml, 2.5M in hexanes) and dry thf (35 ml). The crude product was purified by flash chromatography [fine mesh silica gel; dichloromethane (initially) and 9:1 dichloromethane-methanol (finally)]; to give a dark green solid which was recrystallised (cyclohexane) and dried in vacuo ($P_2O_5$, 0.30 mm Hg, 35° C., 5 hours).

Yield=0.77 g, (58%) mp=100°–102° C.

COMPOUND 34

3-(3-Fluoro-4-dodecyloxyphenyl)propiolic Acid

This compound was prepared using a similar method to that described for compound 31. Quantities: compound 25 (2.48 g, 8.16 mmol), butyllithium (3.3 ml, 2.5M in hexanes) and dry thf (40 ml). The pale yellow solid obtained from flash chromatography was recrystallised (cyclohexane) and dried in vacuo ($P_2O_5$, 0.10 mm Hg, 40° C., 4 hours).

Yield=1.70 g, (60%) mp=89°–93° C.

COMPOUND 35

3-(3-Fluoro-4-tridecyloxyphenyl)propiolic Acid

This compound was prepared using a similar method to that described for compound 31. Quantities: compound 26 (1.71 g, 5.4 mmol), butyllithium (2.2 ml, 2.5M in hexanes) and dry thf (35 ml). The pale yellow solid obtained after flash chromatography was recrystallised (cyclohexane) and dried in vacuo ($P_2O_5$, 0.10 mm Hg, 40° C., 18 hours).

Yield=1.12 g, (57%) mp=91°–94° C.

COMPOUND 36

3-(3-Fluoro-4-tetradecyloxyphenyl)propiolic Acid

This compound was prepared using a similar method to that described for compound 31. Quantities: compound 27 (3.03 g, 9.1 mmol), butyllithium (3.8 ml, 2.5M in hexanes) and dry thf (35 ml). The yellow solid obtained after flash chromatography was recrystallised (cyclohexane-ethyl acetate), washed with petrol (bp 40°–60° C.) (1 ml) and dried in vacuo ($P_2O_5$, 0.10 mm Hg, 45° C., 5 hours).

Yield=2.47 g, (72%) mp=91°–93° C.

COMPOUND 37

3-(3-Fluoro-4-pentadecyloxyphenyl)propiolic Acid

This compound was prepared using a similar method to that described for compound 31. Quantities: compound 28 (2.62 g, 7.57 mmol), butyllithium (3.2 ml, 2.5M in hexanes) and dry thf (50 ml). The yellow solid obtained after flash chromatography was recrystallised (cyclohexane) and dried in vacuo ($P_2O_5$, 0.10 mm Hg, 40° C., 5 hours).

Yield=1.67 g, (56%) mp=95°–97° C.

COMPOUND 38

3-(3-Fluoro-4-hexadecyloxyphenyl)propiolic Acid

This compound was prepared using a similar method to that described for compound 31. Quantities: compound 29 (3.58 g, 9.9 mmol), butyllithium (4.00 ml, 2.5M in hexanes) and dry thf (50 ml). The crude product was purified by flash chromatography [fine mesh silica gel; dichloromethane (initially) and 9:1 dichloromethane-methanol (finally)]; the yellow solid obtained was recrystallised (cyclohexane) and dried in vacuo ($P_2O_5$, 0.30 mm Hg, 30° C., 5 hours).

Yield=2.53 g, (63%) mp=93°–96° C.

COMPOUND 40

4'-Hydroxybiphenyl-4-carboxylic Acid

A mixture of concentrated sulphuric acid (115 ml) and water (115 ml) was added dropwise to a stirred suspension of 4-cyano-4'-hydroxybiphenyl 39 (25.62 g, 131.4 mmol) in glacial acetic acid (400 ml). The mixture was heated under reflux for 48 hours, the cooled reaction mixture was then poured into water (600 ml) with stirring and the white precipitate filtered off. The aqueous filtrate was then washed with diethyl ether (4×70 ml); the combined extracts were then washed with water (50 ml), dried ($MgSO_4$) filtered and evaporated to give a white solid, both crops of product were combined, dried thoroughly and recrystallised (glacial acetic acid) and dried in vacuo ($P_2O_5$, 0.30 mm Hg, 50° C., 5 hours).

Yield=23.49 g, (84%) mp—not recorded

COMPOUND 41

4'-Methoxycarbonyloxybiphenyl-4-carboxylic Acid

Compound 40 (15.02 g, 70.2 mmol) was added slowly to a vigorously stirred solution of sodium hydroxide (8.15 g, 203.8 mmol) in water (300 ml) at –4° C. Methyl chloroformate (10.82 g, 114.5 mmol) was added dropwise and the temperature maintained at 0° C. The resulting white slurry was then stirred under these conditions for a further 4 hours. The pH was then adjusted to 5 using concentrated hydrochloric acid solution (1:1, conc HCl-water) and the voluminous white precipitate filtered off and washed with water. The white solid was dried and recrystallised (glacial acetic acid) and dried in vacuo ($P_2O_5$, 0.20 mm Hg, 40° C., 4 hours).

Yield=14.83 g, (78%) mp=256°–260° C.

COMPOUND 42

(R)-1-Methylheptyl 4'-methoxycarbonyloxybiphenyl-4-carboxylate

Triphenylphosphine (6.80 g, 25.9 mmol) and (S)-octan-2-ol (5.03 g, 38.6 mmol) in dry thf (25 ml) was added dropwise to a stirred mixture of compound 41 (7.03 g, 25.8 mmol) and diethyl azodicarboxylate (4.50 g, 25.9 mmol) in dry thf (40 ml) under nitrogen. The reaction was stirred for a further 24 hours at room temperature. The white precipitate was removed by filtrate through a pad of 'Hyflosupercel', the filtrate was then washed with brine (50 ml), dried ($MgSO_4$), filtered and evaporated to give a white solid. This was purified by flash chromatography [fine mesh silica gel: 5% (v/v) ethyl acetate in petrol (bp 40°–60° C.)] to give a colourless oil which was dried in vacuo ($P_2O_5$, 0.20 mm Hg, RT, 5 hours).

Yield=8.06 g, (81%)

COMPOUND 43

(S)-1-Methylheptyl 4'-methoxycarbonyloxybiphenyl-4-carboxylate

This compound was prepared using a similar method to that described for compound 42. Quantities: triphenylphosphine (6.74 g, 25.7 mmol), (R)-octan-2-ol (5.03 g, 38.7 mmol), compound 41 (7.00 g, 25.7 mmol), diethyl azodicarboxylate (4.50 g, 25.9 mmol) and dry thf (110 ml). The crude product was purified by flash chromatography [fine mesh silica gel; 5% (v/v) ethyl acetate in petrol (bp 40°–60° C.)]; to give a colourless liquid which was dried in vacuo ($P_2O_5$, 0.20 mm Hg, RT, 5 hours).

Yield=7.98 g, (81%)

COMPOUND 44

(R)-1-Methylheptyl 4'-hydroxybiphenyl-4-carboxylate

A solution of compound 42 (8.06 g, 20.9 mmol) in ethanol (30 ml) was added dropwise to a stirred mixture of ammonia (105 ml, 35% solution) and ethanol (180 ml) at room temperature. TLC analysis showed complete reaction after a period of 30 min. The reaction was then poured into water (300 ml) and cooled in 'Cardice', the precipitated product was then filtered off, dried and recystallised (cyclohexane-ethyl acetate, 4:1), the colourless crystals were then dried in vacuo ($P_2O_5$, 0.10 mm Hg, 40° C., 5 hours).

Yield=5.52 g, (81%) mp=84°–87° C.

COMPOUND 45

(S)-1-Methylheptyl 4'-hydroxybiphenyl-4-carboxylate

This compound was prepared using a similar method to that described for compound 44. Quantities compound 43 (7.51 g, 19.6 mmol), ethanol (210 ml) and ammonia (105 ml, 35% solution).

Yield=4.89 g, (77%) mp=87°–89° C.

COMPOUND 46

(R)-1-Methylheptyl 4'-[(2-fluoro-4-dodecyloxyphenyl)propioloyloxy]biphenyl-4-carboxylate Dicyclohexylcarbodiimide (0.31 g, 1.5 mmol) was added to a stirred mixture of compound 30 (0.42 g, 1.2 mmol), compound 44 (0.39 g, 1.2 mmol), 4-N,N-dimethylaminopyridine (0.05 g, 0.4 mmol) in dry dichloromethane (10 ml) at room temperature and then stirred for a further 18 hours. The reaction was diluted with dichloromethane (50 ml) and the precipitate was removed by filtrate through a pad of 'Hyflosupercel' and the filtrate washed successively with water (50 ml), 5% (v/v) acetic acid solution (2×50 ml), water (50 ml) before being dried ($MgSO_4$), filtered and evaporated to give an orange solid. This was purified twice by flash chromatography, first [fine mesh silica gel; 5% (v/v) ethyl acetate in petrol (bp 40°–60° C.)] and then [fine mesh silica gel; 9:1 dichloromethane-petrol (bp 40°–60° C.)] to give a colourless solid which was recrystallised (cyclohexane, twice) and dried in vacuo ($P_2O_5$, 0.20 mm Hg, 50° C., 7 hours).

Yield=0.17 g, (22%)

Phase Transition Temperatures/°C. (on cooling)

$I\ 87.1\ S_A\ 86.8\ S_c^\circ\ 49.8\ K$

Compounds 46–53 have general formula VII, see Table 5.

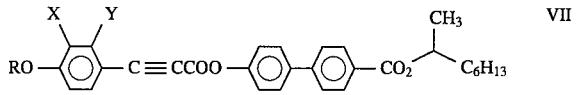

COMPOUND 47

(S)-1-Methylheptyl
4'-[(2-fluoro-4-dodecyloxyphenyl)propioloyloxy]
biphenyl-4-carboxylate This compound was prepared using a similar method to that described for compound 46. Quantities: dicyclohexylcarbodiimide (0.31 g, 1.5 mmol), compound 30 (0.40 g, 1.2 mmol), compound 45 (0.33 g, 1.0 mmol), 4-N,N-dimethylaminopyridine (0.04 g, 0.3 mmol) and dry dichloromethane (16 ml). The crude product was purified twice by flash chromatography, first [fine mesh silica gel; 5% (v/v) ethyl acetate in petrol (bp 40°–60° C.)] and then [fine mesh silica gel; 9:1 dichloromethane-petrol (bp 40°–60° C.)]; to give a white solid which was recrystallised (cyclohexane, three times) and dried in vacuo ($P_2O_5$, 0.30 mm Hg, 40° C., 5 hours).

Yield=0.24 g, (36%)

$I$ 87.1 $S_A$ 86.5 $S_c^*$ 57.6 $K$

COMPOUND 48

(S)-1-Methylheptyl
4'-[(3-fluoro-4-dodecyloxyphenyl)propioloyloxy]
biphenyl-4-carboxylate This compound was prepared using a similar method to that described for compound 46. Quantities: dicyclohexylcarbodiimide (0.37 g, 1.8 mmol), compound 34 (0.57 g, 1.6 mmol), compound 44 (0.51 g, 1.6 mmol), 4-N,N-dimethylaminopyridine (0.06 g, 0.5 mmol) and dry dichloromethane (10 ml). The crude product was purified twice by flash chromatography, first [fine mesh silica gel; 5% (v/v) ethyl acetate in petrol (bp 40°–60° C.)] and then [fine mesh silica gel; 9:1 dichloromethane-petrol (bp 40°–60° C.)]; to give a colourless solid which was recrystallised (cyclohexane, twice) and dried in vacuo ($P_2O_5$, 0.20 mm Hg, 40° C., 5 hours).

Yield=0.31 g, (30%)

$I$ 75.1 $S_c^*$ 74.0 $K$

COMPOUND 49

(S)-1-Methylheptyl
4'-[(3-fluoro-4-dodecyloxyphenyl)propioloyloxy]
biphenyl-4-carboxylate This compound was prepared using a similar method to that described for compound 46. Quantities: dicyclohexylcarbodiimide (0.37 g, 1.8 mmol), compound 34 (0.54 g, 1.6 mmol), compound 45 (0.50 g, 1.6 mmol), 4-N,N-dimethylaminopyridine (0.04 g, 0.3 mmol) and dry dichloromethane (10 ml). The crude product was purified twice by flash chromatography, first [fine mesh silica gel; 5% (v/v) ethyl acetate in petrol (bp 40°–60° C.)] and then [fine mesh silica gel; 9:1 dichloromethane-petrol (bp 40°–60° C.)]; to give a colourless solid which was recrystallised (cyclohexane, three times) and dried in vacuo ($P_2O_5$, 0.10 mm Hg, 40° C., 72 hours).

Yield=0.47 g, (47%)

$I$ 75.5 $S_c^\circ$ 58.2 $K$

COMPOUND 50

(R)-1-Methylheptyl
4'-[(3-fluoro-4-tridecyloxyphenyl)propioloyloxy]
biphenyl-4-carboxylate This compound was prepared using a similar method to that described for compound 46. Quantities: dicyclohexylcarbodiimide (0.54 g, 2.62 mmol), compound 35 (0.56 g, 1.6 mmol), compound 44 (0.51 g, 1.6 mmol), 4-N,N-dimethylaminopyridine (0.05 g, 0.4 mmol) and dry dichloromethane (10 ml). The crude product was purified twice by flash chromatography, first [fine mesh silica gel; 5% (v/v) ethyl acetate in petrol (bp 40°–60° C.)] and then [fine mesh silica gel; 9:1 dichloromethane-petrol (bp 40°–60° C.)]; to give a colourless solid which was recrystallised (cyclohexane, twice) and dried in vacuo ($P_2O_5$, 0.10 mm Hg, 50° C., 6 hours).

Yield=0.16 g, (15%)

$I$ 74.6 $S_c^\circ$ 66.5 $K$

COMPOUND 51

(S)-1-Methylheptyl
4'-[(3-fluoro-4-tridecyloxyphenyl)propioloyloxy]
biphenyl-4-carboxylate This compound was prepared using a similar method to that described for compound 46. Quantities: dicyclohexylcarbodiimide (0.40 g, 1.9 mmol), compound 35 (0.58 g, 1.6 mmol), compound 45 (0.51 g, 1.6 mmol), 4-N,N-dimethylaminopyridine (0.05 g, 0.4 mmol) and dry dichloromethane (10 ml). The crude product was purified twice by flash chromatography, first [fine mesh silica gel; 5% (v/v) ethyl acetate in petrol (bp 40°–60° C.)] and then [fine mesh silica gel; 9:1 dichloromethane-petrol (bp 40°–60° C.)]; to give a colourless solid which was recrystallised (cyclohexane, twice) and dried in vacuo ($P_2O_5$, 0.10 mm Hg, 40° C., 8 hours).

Yield=0.13 g, (12%)

$I$ 74.2 $S_c^\circ$ 63.5 $K$

COMPOUND 52

(R)-1-Methylheptyl
4'-[(3-fluoro-4-tetradecyloxyphenyl)propioloyloxy]
biphenyl-4-carboxylate This compound was prepared using a similar method to that described for compound 46. Quantities: dicyclohexylcarbodiimide (0.35 g, 1.7 mmol), compound 36 (0.59 g, 1.6 mmol), compound 44 (0.50 g, 1.5 mmol), 4-N,N-dimethylaminopyridine (0.04 g, 0.3 mmol) and dry dichloromethane (10 ml). The crude product was purified twice by flash chromatography, first [fine mesh silica gel; 5% (v/v) ethyl acetate in petrol (bp 40°–60° C.)] and then [fine mesh silica gel; 9:1 dichloromethane-petrol (bp 40°–60° C.)]; to give a colourless solid which was recrystallised (cyclohexane, twice) and dried in vacuo ($P_2O_5$, 0.10 mm Hg, 40° C., 6 hours).

Yield=0.15 g, (14%)

$I$ 75.4 $S_c^\circ$ 49.6 $K$

COMPOUND 53

(S)-1-Methylheptyl 4'-[(3-fluoro-4-tetradecyloxyphenyl)propioloyloxy] biphenyl-4-carboxylate This compound was prepared using a similar method to that described for compound 46. Quantities: dicyclohexylcarbodiimide (0.37 g, 1.8 mmol), compound 36 (0.58 g, 1.5 mmol), compound 45 (0.50 g, 1.5 mmol), 4-N,N-dimethylaminopyridine (0.03 g, 0.25 mmol) and dry dichloromethane (10 ml). The crude product was purified twice by flash chromatography, first [fine mesh silica gel; 5% (v/v) ethyl acetate in petrol (bp 40°–60° C.)] and then [fine mesh silica gel; 9:1 dichloromethane-petrol (bp 40°–60° C.)]; to give a colourless solid which was recrystallised (cyclohexane, twice) and dried in vacuo ($P_2O_5$, 0.30 mm Hg, 40° C., 17 hours).

Yield=0.18 g, (17%)

*I* 75.5 $S_c°$ 62.7 *K*

Compounds of formula I may be mixed with a wise range of hosts, for example smectic hosts to form a useful liquid crystal composition. Such compositions can have a range of Ps values. Compounds of formula I may be mixed with one or more of the types of hosts VIII–XIII. These different types of hosts maybe mixed together to which the compound of general formula I may also be added.

Typical hosts include:
The compounds described in PCT/GB86/00040, eg of formula VIII

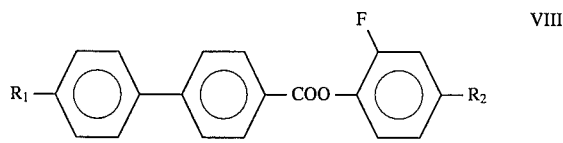

where $R_1$ and $R_2$ are independently $C_3$–$C_{12}$ alkyl or alkoxy.

The fluoro-terphenyls described in EPA 84304894.3 and GBA 8725928, eg of formula IX

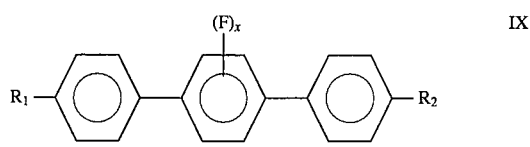

where $R_1$ and $R_2$ are independently $C_3$–$C_{12}$ alkyl or alkoxy, x is 1 and F may be on any of the available substitution positions on the phenyl ring specified.

The difluoro-terphenyls described in GBA 8905422.5, eg of formula X

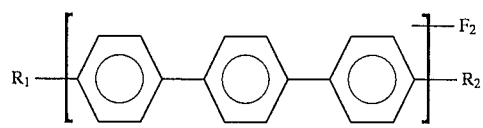

where $R_1$ and $R_2$ are independently $C_3$–$C_{12}$ alkyl or alkoxy.

The phenyl-pyrimidines described in WO 86/00087, eg of formula XI

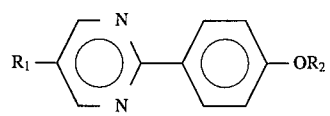

including those compounds were $R_1$ is $C_3$–$C_{12}$ aklyl and $R_2$ is given by the general formula $(CH_2)_n$—$CHXCH_2CH_3$, where n is 1 to 5 and X is CN or Cl.

The compounds described by R. Eidenschink et. al. in Cyclohexanederivative mit Getilteneten Smedtischen Phasen at the 16th Freiberg LIquid Crystal Conference, Freiberg, Germany, p8. Available from E. Merck Ltd., German, eg of formula XII.

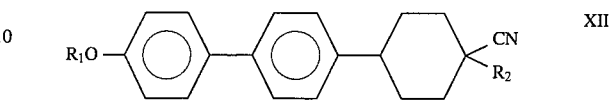

including those compounds where $R_1$ and $R_2$ are independently $C_1$–$C_{15}$ alkyl.

The difluoro-phenyl pyrimidines described at the 2nd International Symposium on Ferroelectric Liquid Crystals, Göteborg, Sweden, June 1989 by Reiffenrath et. al., eg of formula XIII

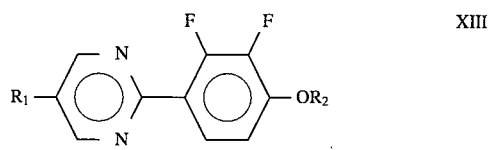

including those compounds where $R_1$ and $R_2$ are independently $C_3$–$C_9$ alkyl.

Figure 2:
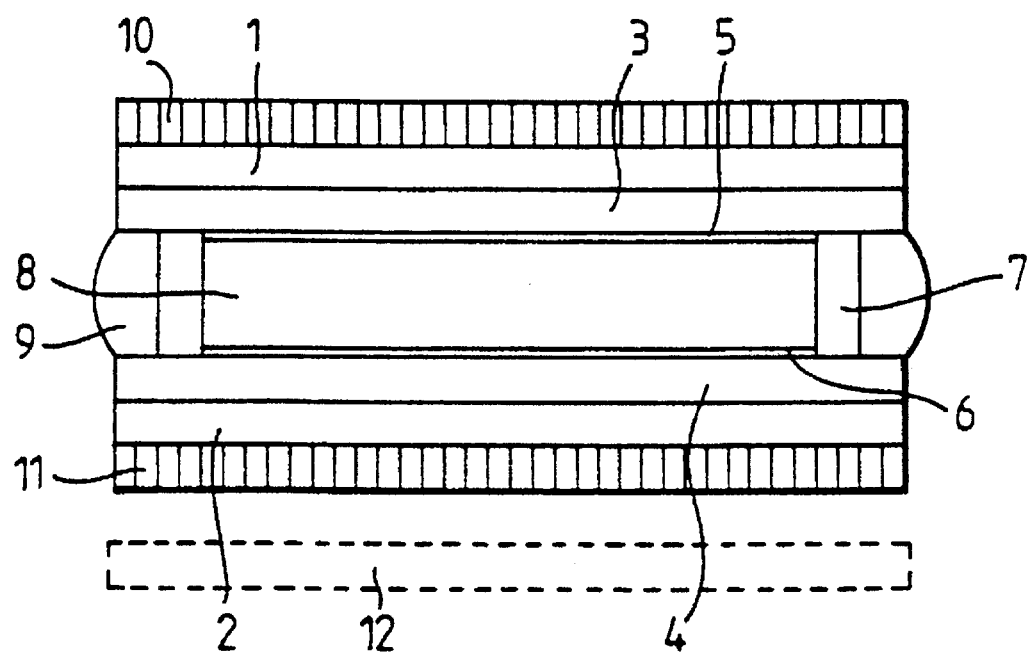
FIG. 2 illustrates a liquid crystal device.
Figure 3:
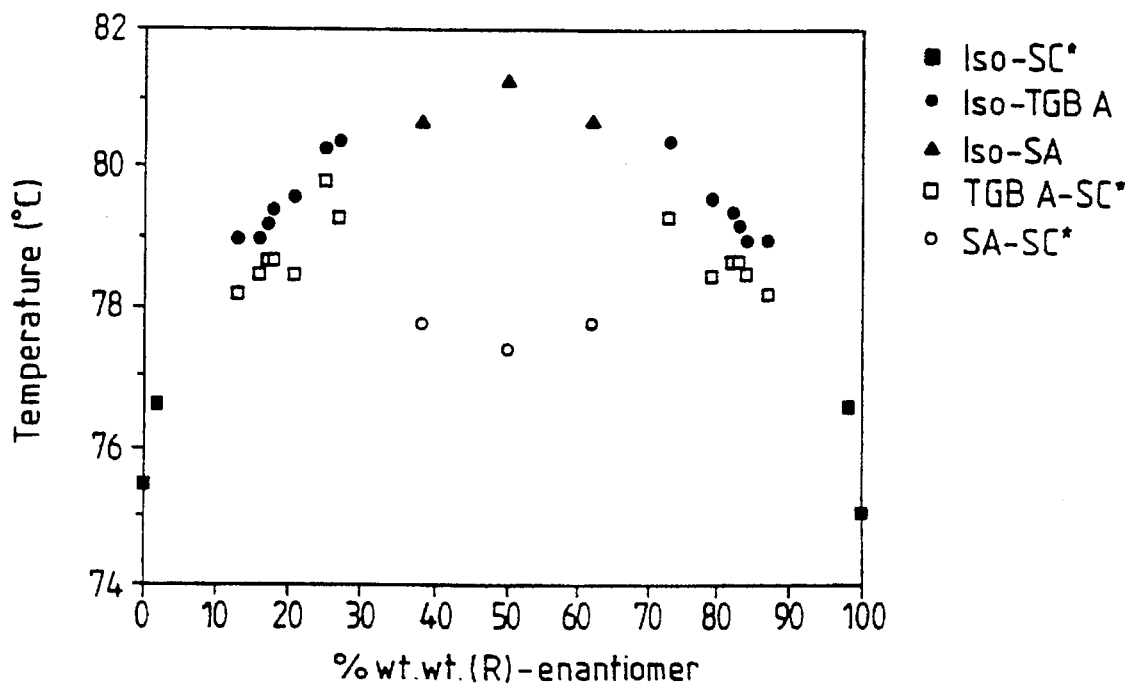
FIGS. 3–12 are phase diagrams for compounds 46–65 (R) and (S) mixtures.
Figure 4:
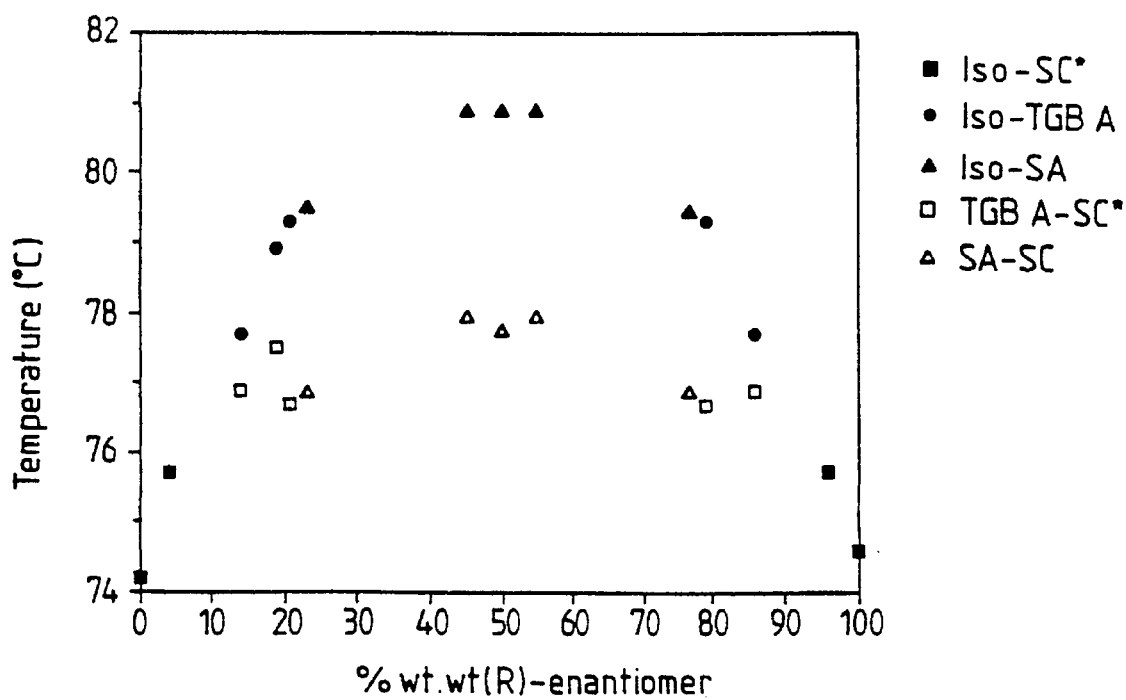
Figure 5:
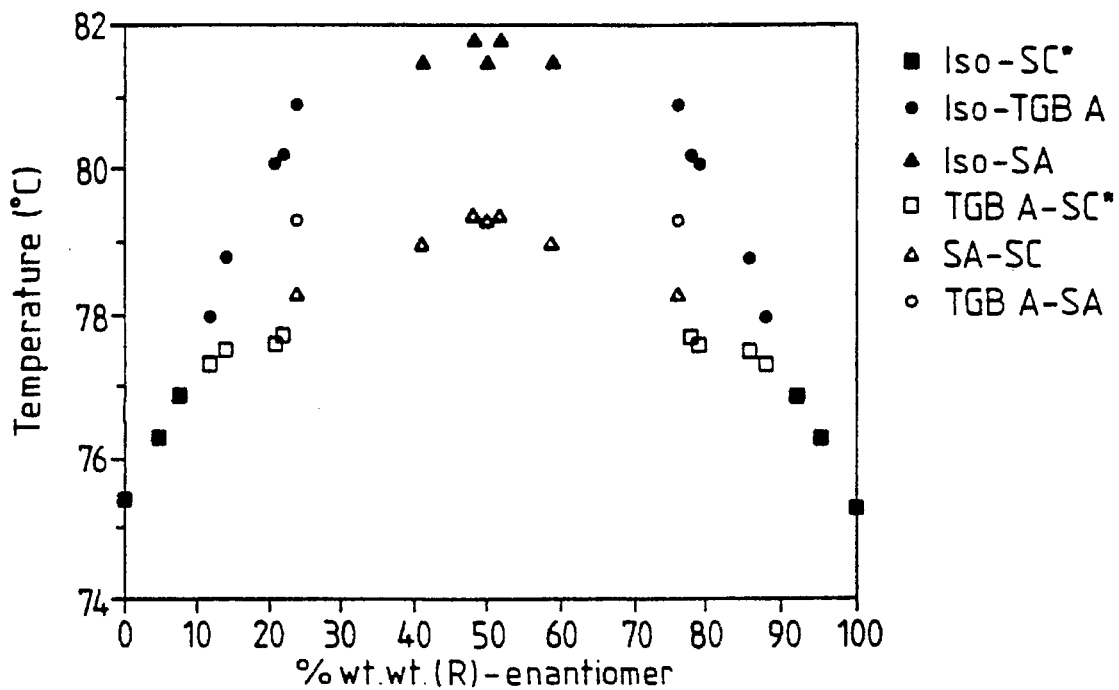
Figure 6:
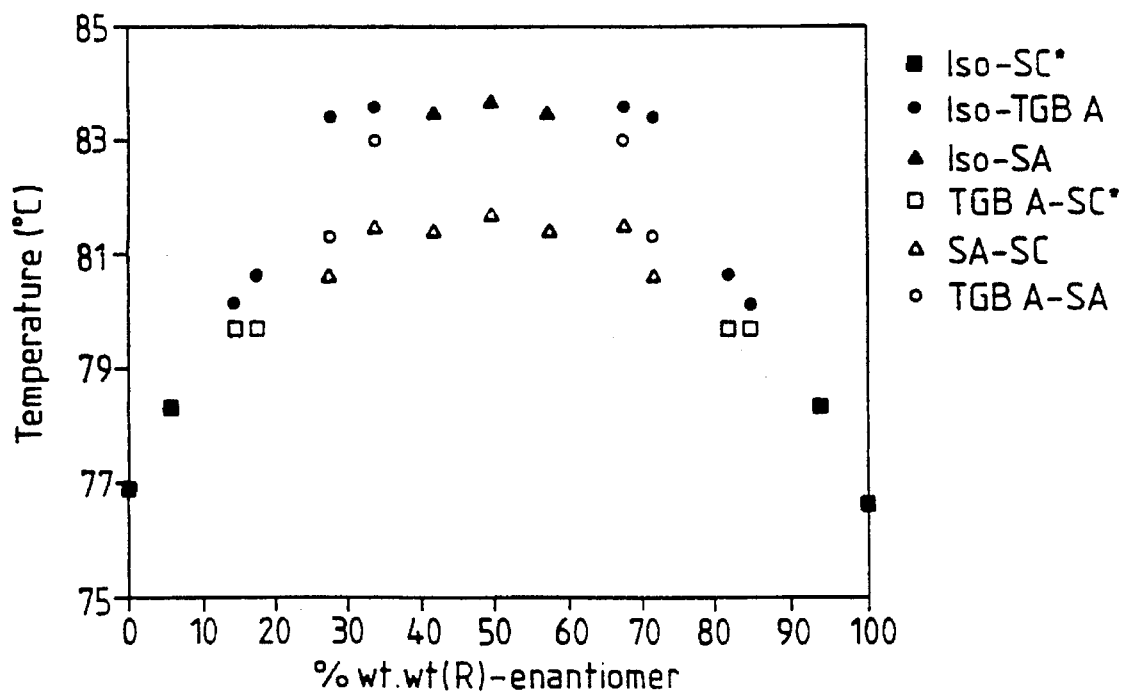
Figure 7:
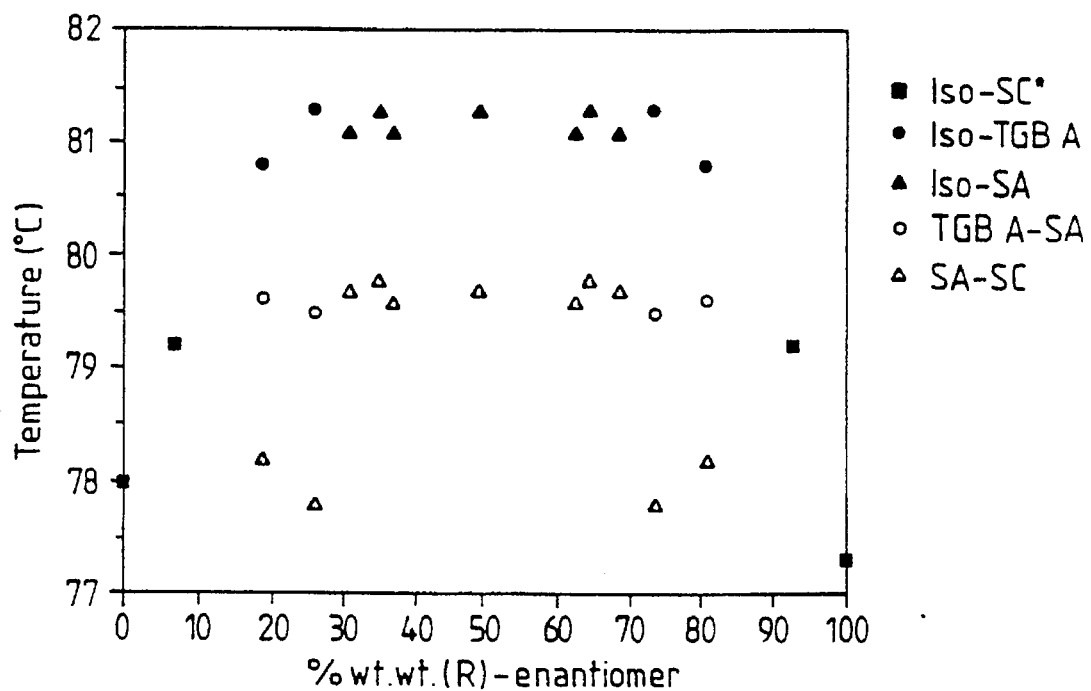
Figure 8:
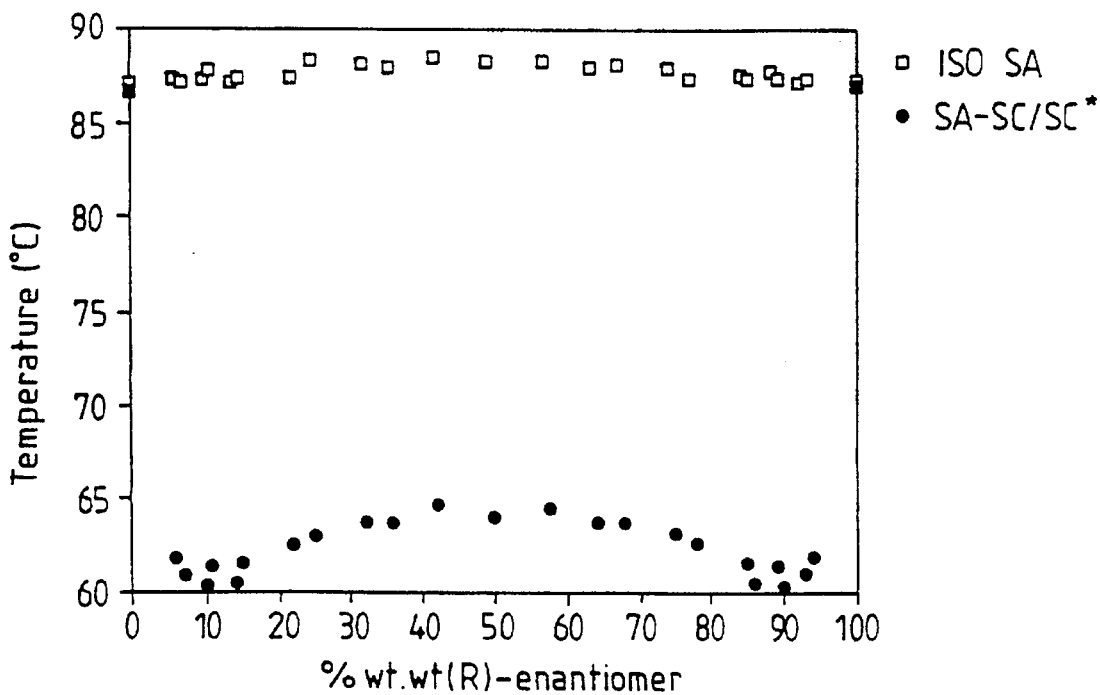
Figure 9:
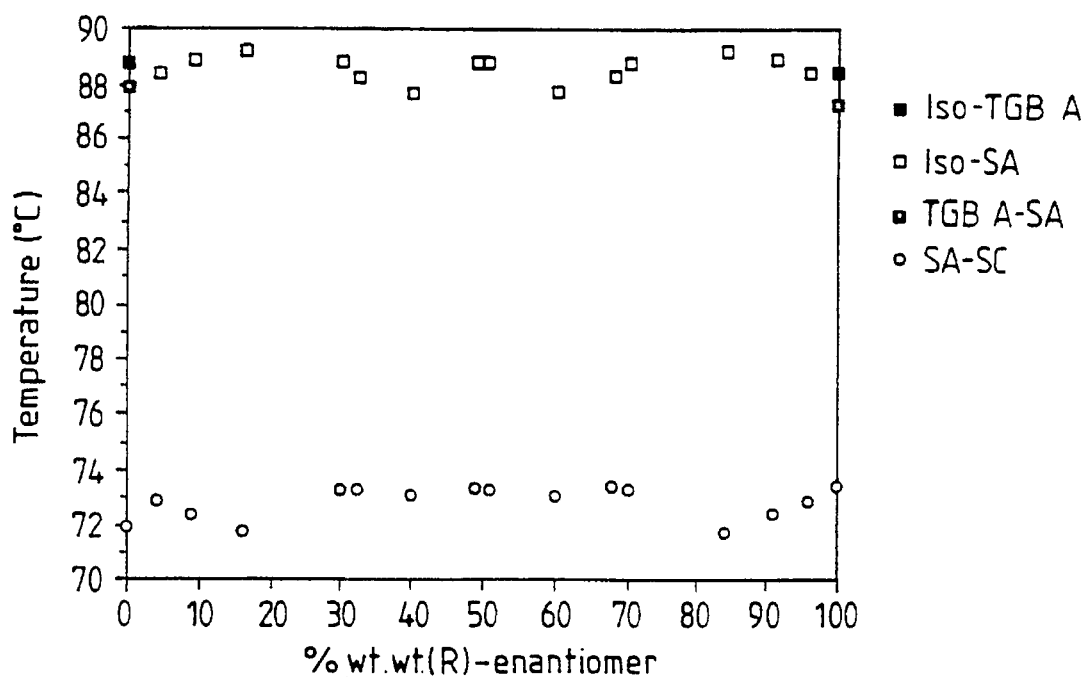
Figure 10:
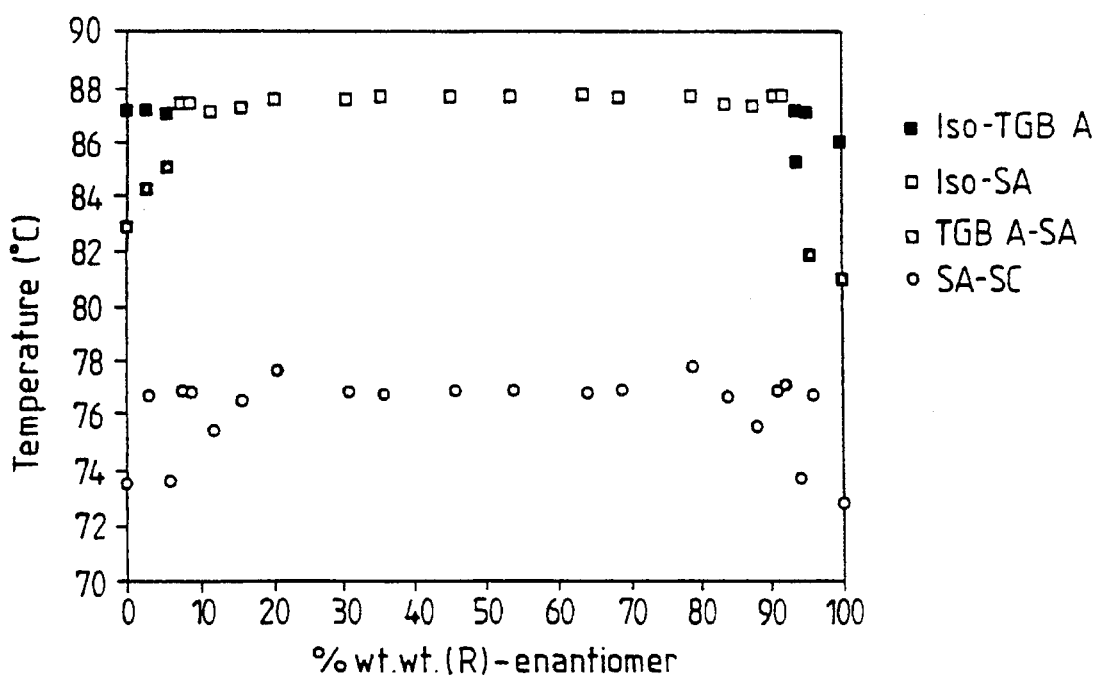
Figure 11:
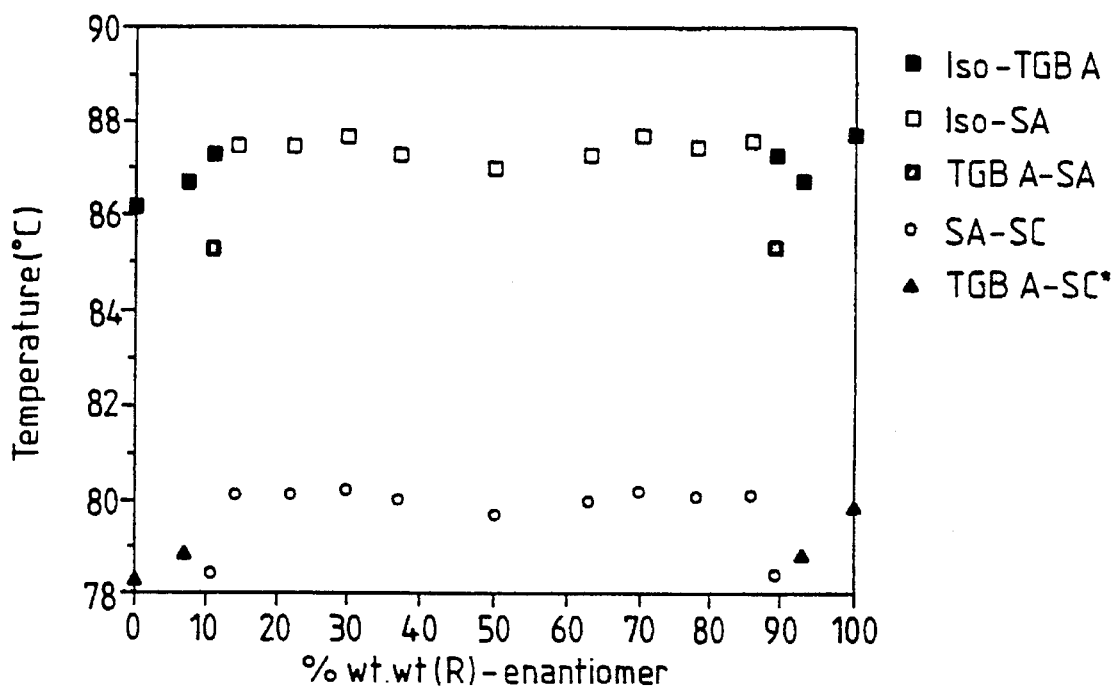
Figure 12:
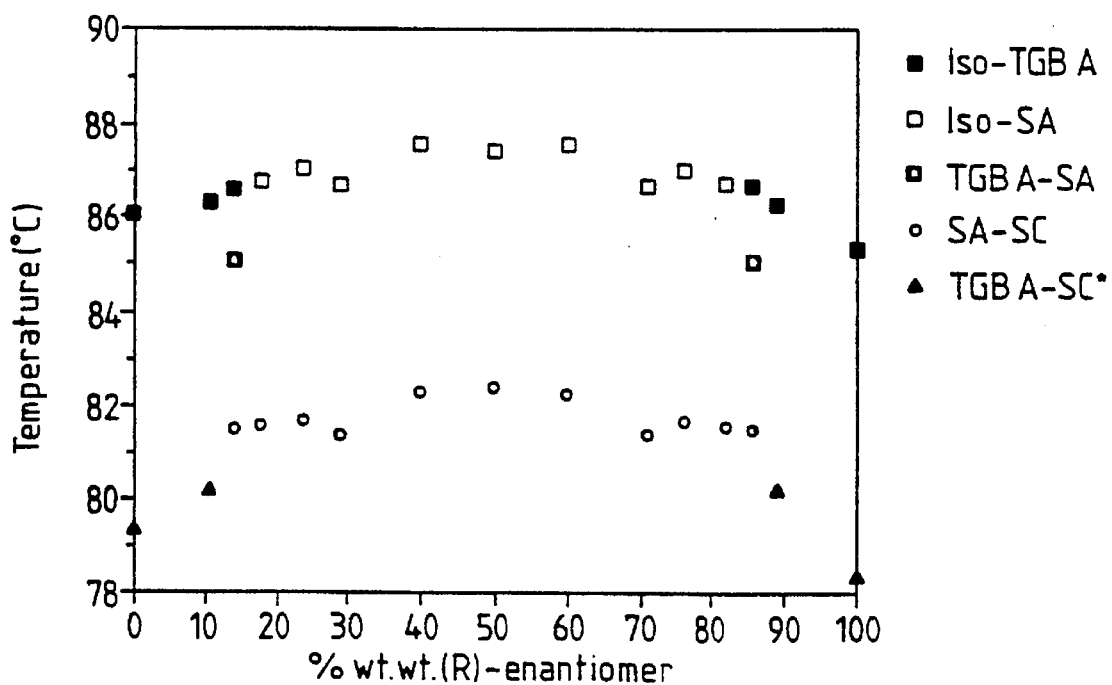

An example of the use of a compound of Formula I in a liquid crystal material and device embodying the present invention will now be described with reference to FIG. 2.

The liquid crystal device consists of two transparent plates, 1 and 2, in this case made from glass. These plates are coated on their internal face with transparent conducting electrodes 3 and 4. An alignment layer is introduced onto the internal faces of the cell so that a planar orientation of the molecules making up the liquid crystalline material will be approximately parallel to the glass plates 1 and 2. This is done by coating the glass plates 1, 2 complete with conducting electrodes 3, 4 with layers of film 5 and 6 of a suitable polymer, eg polyimide. The electrodes 3, 4 may be formed into row and column electrodes so that the intersections between each column and row form an x, y matrix of addressable elements or pixels. Prior to the construction of the cell the films 5, 6 are rubbed with a soft tissue in a given direction, th rubbing directions being arranged parallel upon construction of the cell. A spacer 7 eg of polymethyl methacrylate separates the glass plates 1 and 2 to a suitable distance eg 2 microns. Liquid crystal material 8 is introduced between glass plates 1, 2 by filling the space in between them. The spacer 7 is sealed with an adhesive 9 in a vacuum using an existing technique. Polarisers 10, 11 are arranged in front of and behind the cell.

The device may operate in a transmissive or reflective mode. In the former, light passing through the device, eg from a tungsten bulb, is selectively transmitted or blocked to form the desired display. In the reflective move a mirror (12) is placed behind the second polariser 11 to reflect ambient light back through the cell and two polarisers. By making the mirror partly reflecting the device may be operated both in a transmissive and reflective mode.

Tables 8–11 give values for the spontaneous polarisation (Pa/nC/cm²) over a range of temperatures (°C.) for a number of the compounds described by general formula I. The compounds of formula I may be added to host materials. Table 12 gives values of the spontaneous polarisation (Ps/nC/cm²) over a range of temperatures (°C.) when it is mixed 10% by weight with host material H1. H1 is a 1:1:1 mixture of the following:

$R_1=C_8H_{17}$, $R_2=C_5H_{11}$ $R_1=OC_8H_{17}$, $R_2=C_5H_{11}$ $R_1=OC_8H_{17}$, $R_2=C_7H_{15}$

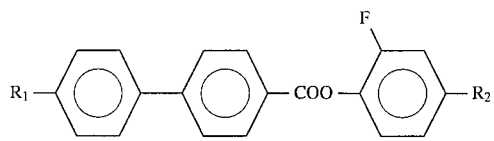

The host is a commercially available host and is widely used in ferroelectric liquid crystal mixtures.

The Ps was measured in a 6 μm polyimide (PI) parallel cell using a diamant bridge and applying a sine wave at 30 Hz.

Figure 13:
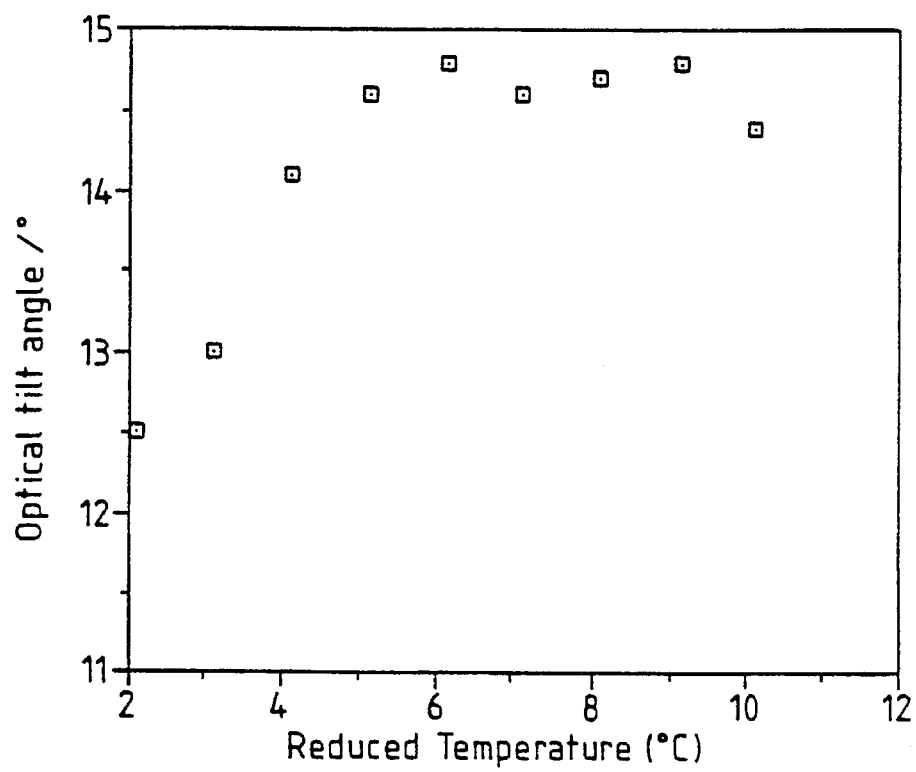
FIGS. 13 and 14 are graphs of optical tilt angle/° versus reduced temperature/°C. for compounds 52 and 56 respectively.
Figure 14:
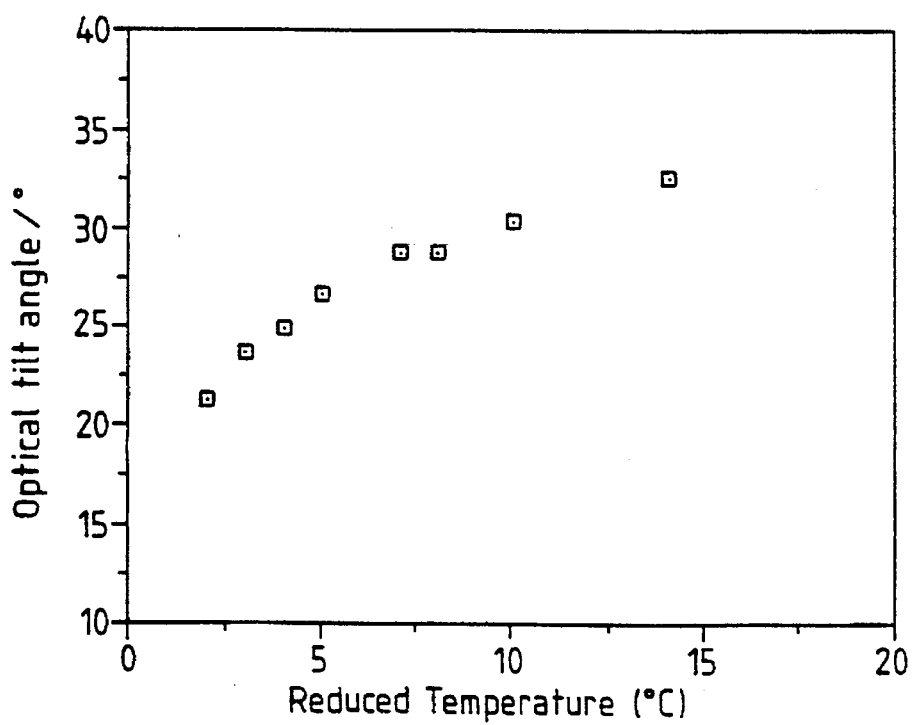

The optical tilt angle measurements detailed in FIGS. 13 and 14 show the dependence of the optical tilt angle of the $S_c^*$ phase with reduced temperature and the studies were performed in 3.6 μm thick polyimide coated cells.

FIGS. 3–12 are phase diagrams for compounds 48/49; 50/51; 52/53; 60/61; 64/65; 46/47; 54/55; 56/57; 58/59; 62/63.

TABLE 1

| Compound | R | X | Y |
|---|---|---|---|
| 3 | $C_{12}H_{25}$ | H | F |
| 4 | $C_{13}H_{27}$ | H | F |
| 5 | $C_{14}H_{29}$ | H | F |
| 6 | $C_{15}H_{31}$ | H | F |
| 7 | $C_{12}H_{25}$ | F | H |
| 8 | $C_{13}H_{27}$ | F | H |
| 9 | $C_{14}H_{29}$ | F | H |
| 10 | $C_{15}H_{31}$ | F | H |
| 11 | $C_{16}H_{33}$ | F | H |

TABLE 2

| Compound | R | X | Y |
|---|---|---|---|
| 12 | $C_{12}H_{25}$ | H | F |
| 13 | $C_{13}H_{27}$ | H | F |
| 14 | $C_{14}H_{29}$ | H | F |
| 15 | $C_{15}H_{31}$ | H | F |
| 16 | $C_{12}H_{25}$ | F | H |
| 17 | $C_{13}H_{27}$ | F | H |
| 18 | $C_{14}H_{29}$ | F | H |
| 19 | $C_{15}H_{31}$ | F | H |
| 20 | $C_{16}H_{33}$ | F | H |

TABLE 3

| Compound | R | X | Y |
|---|---|---|---|
| 21 | $C_{12}H_{25}$ | H | F |
| 22 | $C_{13}H_{27}$ | H | F |
| 23 | $C_{14}H_{29}$ | H | F |
| 24 | $C_{15}H_{31}$ | H | F |
| 25 | $C_{12}H_{25}$ | F | H |
| 26 | $C_{13}H_{27}$ | F | H |
| 27 | $C_{14}H_{29}$ | F | H |
| 28 | $C_{15}H_{31}$ | F | H |
| 29 | $C_{16}H_{33}$ | F | H |

TABLE 4

| Compound | R | X | Y |
|---|---|---|---|
| 30 | $C_{12}H_{25}$ | H | F |
| 31 | $C_{13}H_{27}$ | H | F |
| 32 | $C_{14}H_{29}$ | H | F |
| 33 | $C_{15}H_{31}$ | H | F |
| 34 | $C_{12}H_{25}$ | F | H |
| 35 | $C_{13}H_{27}$ | F | H |
| 36 | $C_{14}H_{29}$ | F | H |
| 37 | $C_{15}H_{31}$ | F | H |
| 38 | $C_{16}H_{33}$ | F | H |

TABLE 5

| Compound | R | X | Y |
|---|---|---|---|
| 46 (R)* | $C_{12}H_{25}$ | H | F |
| 47 (S) | $C_{12}H_{25}$ | H | F |
| 48 (R) | $C_{12}H_{25}$ | F | H |
| 49 (S) | $C_{12}H_{25}$ | F | H |
| 50 (R) | $C_{13}H_{27}$ | F | H |
| 51 (S) | $C_{13}H_{27}$ | F | H |
| 52 (R) | $C_{14}H_{29}$ | F | H |
| 53 (S) | $C_{14}H_{29}$ | F | H |

*optical isomer

In a manner similar to that for compounds 46–54, compounds 54–65 were also synthesised. Compounds 54–65 have the same general formula as those compounds in Table 5 and are presented in Table 6.

TABLE 6

| Compound | R | X | Y |
|---|---|---|---|
| 54 (R)* | $C_{13}H_{27}$ | H | F |
| 55 (S) | $C_{13}H_{27}$ | H | F |
| 56 (R) | $C_{14}H_{29}$ | H | F |
| 57 (S) | $C_{14}H_{29}$ | H | F |
| 58 (R) | $C_{15}H_{31}$ | H | F |
| 59 (S) | $C_{15}H_{31}$ | H | F |
| 60 (R) | $C_{15}H_{31}$ | F | H |
| 61 (S) | $C_{15}H_{31}$ | F | H |
| 62 (R) | $C_{16}H_{33}$ | H | F |
| 63 (S) | $C_{16}H_{33}$ | H | F |
| 64 (R) | $C_{16}H_{33}$ | F | H |
| 65 (S) | $C_{16}H_{33}$ | F | H |

*optical isomer

The phase transition data for these compounds is presented in Table 7 and is as follows:

TABLE 7

| Compound | Phase Transitions/°C |
|---|---|
| 54: | I 88.4 $TGB_A$ 87.3 $S_A$ 73.4 $S_c^\circ$ |
| 55: | I 88.8 $TGB_A$ 88.0 $S_A$ 72.0 $S_c^\circ$ |
| 56: | I 85.8 $TGB_A$ 80.8 $S_A$ 72.6 $S_c^\circ$ |
| 57: | I 87.1 $TGB_A$ 82.9 $S_A$ 73.5 $S_c^\circ$ |
| 58: | I 87.7 $TGB_A$ 79.9 $S_c^\circ$ |
| 59: | I 86.2 $TGB_A$ 78.3 $S_c^\circ$ |
| 60: | I 76.6 $S_c^\circ$ |
| 61: | I 76.9 $S_c^\circ$ |
| 62: | I 85.4 $TGB_A$ 78.4 $S_c^\circ$ |
| 63: | I 86.1 $TGB_A$ 79.4 $S_c^\circ$ |
| 64: | I 77.3 $S_c^\circ$ |
| 65: | I 78.0 $S_c^\circ$ |

$TGB_A$ = Twisted grain boundary A phase.

TABLE 8

| Temp/°C. | Ps/nC/cm² |
|---|---|
| 74 | 23.6 |
| 72 | 40.5 |
| 70 | 47.6 |
| 65 | 63.0 |
| 60 | 68.7 |
| 55 | 74.8 |
| 50 | 79.0 |
| 45 | 77.5 |
| 40 | 66.5 |

Compound 56: 5.9 µm PI parallel cell.

TABLE 9

| Temp/°C. | Ps/nC/cm² |
|---|---|
| 75 | 42.2 |
| 70 | 59.0 |
| 65 | 67.7 |
| 60 | 73.5 |
| 55 | 73.0 |
| 50 | 69.0 |

Compound 58: 6.0 µm PI parallel cell.

TABLE 10

| Temp/°C. | Ps/nC/cm² |
|---|---|
| 76 | 50.5 |
| 74 | 60.0 |
| 72 | 66.0 |
| 70 | 71.0 |
| 65 | 81.0 |
| 60 | 87.0 |

Compound 62: 6.1 µm PI parallel cell.

TABLE 11

| Temp/°C. | Ps/nC/cm² |
|---|---|
| 73 | 69.4 |
| 72 | 73.1 |
| 70 | 79.1 |
| 65 | 90.0 |
| 63 | 93.2 |
| 60 | 98.1 |
| 55 | 102.5 |
| 53 | 104.3 |
| 50 | 106.0 |
| 45 | 105.0 |
| 43 | 100.4 |
| 40 | 99.6 |

Compound 64: 5.5 µm PI parallel cell.

TABLE 12

| Temp/°C. | Ps/nC/cm² |
|---|---|
| 81 | 0.3 |
| 80 | 0.5 |
| 75 | — |
| 72 | 1.1 |
| 70 | 1.3 |
| 60 | 1.6 |
| 50 | 1.5 |
| 40 | 1.3 |

Compound 64 10% by weight in H1: 5.1 µm PI parallel cell.

We claim:

1. A compound having formula I

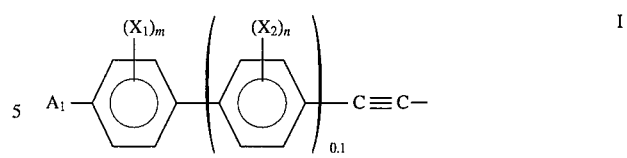
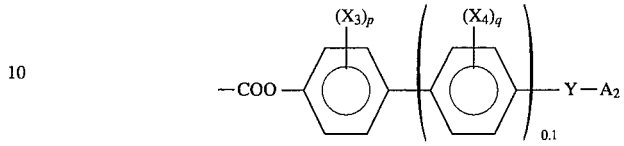

where $A_1$ is selected from alkyl, alkoxy or alkenyl and contains 3–20 carbon atoms, $X_1$, $X_2$, $X_3$ and $X_4$ are independently selected from the halogen group; m, n, p and q are independently 0, 1, 2, 3 or 4 such that $m+n+p+q \neq 0$; Y is selected from O and COO; $A_2$ is an end group of formula II

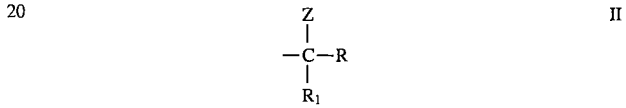

where Z is selected from halogen, $CH_3$, CN, $CF_3$, $CHF_2$; R is a linear or branched alkyl group containing 2–15 carbon atoms or H; $R_1$ is a linear or branched alkyl group containing 1–5 carbon atoms or H.

2. A compound according to claim 1 wherein $A_1$ contains 6–16 carbon atoms; R contains 3–10 atoms; Z is $CH_3$ or CN; $R_1$ is H; X is F and each of m, n, p and/or q is independently 0, 1 or 2 such that m+n+p+q=1 or 2.

3. A compound according to claim 1 wherein $A_1$ contains 9–15 carbon atoms; R contains 5–7 atoms; Z is $CH_3$ or CN; $R_1$ is H; X is F and each of m, n, p and/or q is independently 0, 1 or 2 such that m+n+p+q=1 or 2.

4. A liquid crystal device comprising a layer of liquid crystal material contained between two spaced cell walls each bearing electrode structures and surface treated on facing surfaces to align liquid structures and surface treated on facing surfaces to align liquid crystal material molecules, characterised in that the liquid crystal material includes the compound as described in claim 1.

5. A liquid crystal mixture containing any of the compounds of claim 1 and a host material of the following general formula

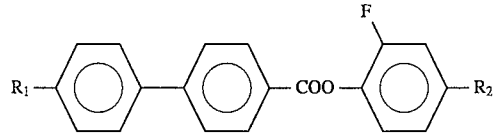

where $R_1$ and $R_2$ are independently $C_3$–$C_{12}$ alkyl or alkoxy.

6. A liquid crystal mixture containing any of the compounds of claim 1 and a host material of the following general formula

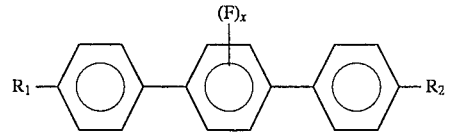

where $R_1$ and $R_2$ are independently $C_3$–$C_{12}$ alkyl or alkoxy, x is 1 and F is on any one of the available substitution positions on the phenyl ring specified.

7. A liquid crystal mixture containing any of the compounds of claim 1 and a host material of the following general formula

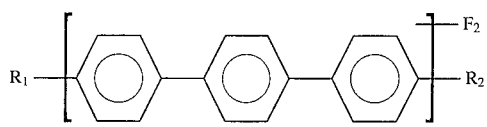

where $R_1$ and $R_2$ are independently $C_3$–$C_{12}$ alkyl or alkoxy.

8. A liquid crystal mixture containing any of the compounds of claim 1 and a host material of the following general formula

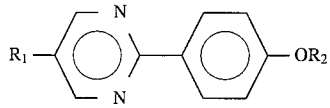

where $R_1$ is $C_3$–$C_{12}$ alkyl and $R_2$ is given by the general formula $(CH_2)_n$—$CHXCH_2CH_3$, where n is 1 to 5 and X is CN or Cl.

9. A liquid crystal mixture containing any of the compounds of claim 1 and a host material of the following general formula

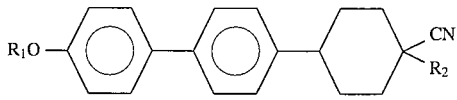

where $R_1$ and $R_2$ are independently $C_1$–$C_{15}$ alkyl or alkoxy.

10. A liquid crystal mixture containing any of the compounds of claim 1 and a host material of the following general formula

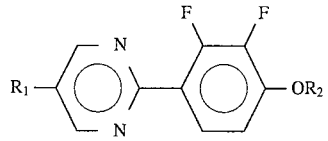

where $R_1$ and $R_2$ are independently $C_3$–$C_9$ alkyl or alkoxy.

11. A liquid crystal device comprising the liquid crystal mixture as in any one of claims 5–10.

* * * * *